(12) United States Patent
Cheng et al.

(10) Patent No.: US 7,667,089 B2
(45) Date of Patent: Feb. 23, 2010

(54) TRANSGENIC MAMMAL SECRETING B-DOMAIN DELETED HUMAN FVII IN ITS MILK

(75) Inventors: Winston T. K. Cheng, Taipei (TW); Chuan-Mu Chen, Taichung (TW); Shwu-Wha Lin, Taipei (TW); Chih-Hong Wang, Taichung (TW); Chih-Jen Lin, Taipei (TW); Shinn-Chih Wu, Miaoli (TW)

(73) Assignee: National Chung Hsing University, Taichung (TW)

( * ) Notice: Subject to any disclaimer, the term of this patent is extended or adjusted under 35 U.S.C. 154(b) by 0 days.

(21) Appl. No.: 10/820,777

(22) Filed: Apr. 9, 2004

(65) Prior Publication Data

US 2005/0229261 A1 Oct. 13, 2005

(51) Int. Cl.
*C12P 21/00* (2006.01)
*A01K 67/027* (2006.01)
*C12N 15/00* (2006.01)

(52) U.S. Cl. ............................... 800/14; 800/4; 800/15; 800/16; 800/17; 800/18; 800/21

(58) Field of Classification Search .................... 800/7, 800/8–18, 21
See application file for complete search history.

(56) References Cited

U.S. PATENT DOCUMENTS 5,633,076 A * 5/1997 DeBoer et al. ............... 800/25
6,255,554 B1 * 7/2001 Lubon et al. ................. 800/14

FOREIGN PATENT DOCUMENTS

WO WO 9800541 A2 * 1/1998

OTHER PUBLICATIONS

Niemann et al, Animal Reproduction Science, 79:291-317, 2003.*
Houdebine et al, Transgenic Research, 9:305-320, 2000.*
Chen et al, Transgenic Research, 11:257-268, 2002.*
Niemann et al, Transgenic Research, 8:237-247.*
Paleyanda et al, Nature Biotechnology, 15:971-975, 1997.*
Hiripi et al, DNA and Cell Biology, 22:41-45, 2003.*
Soukharev et al, Blood Cells, Molecules and Diseases, 28:234-248, 2002.*
Toole (PNAS, Aug. 1986, vol. 83, p. 5939-5942).*
Pittman (Blood, 1993, vol. 81, p. 2925-2935).*

* cited by examiner

*Primary Examiner*—Michael C. Wilson
(74) *Attorney, Agent, or Firm*—Panitch Schwarze Belisario & Nadel LLP

(57) ABSTRACT

Hemophilia A is one of the major inherited bleeding disorders caused by a deficiency or abnormality in coagulation factor VIII (FVIII). Hemophiliacs have been treated with whole plasma or purified FVIII concentrates. The risk of transmitting blood-borne viruses and the cost of highly purified FVIII are the major factors that restrict prophylaxis in hemophilia therapy. One of the challenges created by the biotechnology revolution is the development of methods for the economical production of highly purified proteins in large scales. The present invention provides improved mammary expression cassettes useful for the expression of genes at high levels in the milk of transgenic animals. In particular, the present invention provides recombinant signal peptide sequences derived from a-lactalbumin and aS1-casein milk genes suitable for leading protein secretion in the mammary gland. These gene cassettes are capable of delivering different transgenic constructs which result in the production of full-length or B domain-deleted therapeutic levels of biologically active human FVIII in the transgenic animals in vivo. Within the scope of the invention are also method for producing the transgenic non-human mammal, such as mouse, rat, rabbit, goat, sheep, pig and bovine species, capable of expressing human FVIII, and methods of making milk and methods of identifying protein from the transgenic milk.

2 Claims, 9 Drawing Sheets
(2 of 9 Drawing Sheet(s) Filed in Color)

| NPP conc. | aPTT clotting time (s) |
|---|---|
| 50% | 57.7 |
| 20% | 71.9 |
| 10% | 79.0 |
| 5% | 88.9 |
| 2% | 103.2 |

| aPTT clotting time (sec) | Tg-201 goat | | Normal goat | |
|---|---|---|---|---|
| | Day 3 | Day 22 | Day 3 | Day 22 |
| Full milk | 64.4 | 65.7 | 168.1 | 167.6 |
| Defat milk | 59.9 | 68.7 | 173.3 | 169.4 |

SEQUENCE LISTING

<160> NUMBER OF SEQ ID NOS: 15

<210> SEQ ID NO 1
<211> LENGTH: 63
<212> TYPE: DNA
<213> ORGANISM: Artificial
<220> FEATURE:
<223> OTHER INFORMATION: Synthetic

<400> SEQUENCE: 1
atgatgtcct tgtctctct gctcctggta ggcatcctat tccatgccac ccaggctgtt    60
aac                                                                 63

<210> SEQ ID NO 2
<211> LENGTH: 50
<212> TYPE: DNA
<213> ORGANISM: Artificial
<220> FEATURE:
<223> OTHER INFORMATION: Synthetic

<400> SEQUENCE: 2
atgaaacttc tcatccttac ctgtcttgtg gctgttgctg ccaggttaac                50

<210> SEQ ID NO 3
<211> LENGTH: 22
<212> TYPE: DNA
<213> ORGANISM: Homo sapiens

<400> SEQUENCE: 3
ggttaactgc caccagaaga ta                                             22

<210> SEQ ID NO 4
<211> LENGTH: 20
<212> TYPE: DNA
<213> ORGANISM: Homo sapiens

<400> SEQUENCE: 4
aagcttcttg gttcaatggc                                                20

<210> SEQ ID NO 5
<211> LENGTH: 25
<212> TYPE: DNA
<213> ORGANISM: Homo sapiens

<400> SEQUENCE: 5
aagcttgaaa cgccatcaac gggaa                                          25

<210> SEQ ID NO 6
<211> LENGTH: 24
<212> TYPE: DNA
<213> ORGANISM: Homo sapiens

<400> SEQUENCE: 6
ctcgagcctc agtagaggtc ctgt                                           24

<210> SEQ ID NO 7
<211> LENGTH: 20
<212> TYPE: DNA
<213> ORGANISM: Homo sapiens

<400> SEQUENCE: 7
ctctcttgtc atcctcttcc                                                20

-continued

```
<210> SEQ ID NO 8
<211> LENGTH: 21
<212> TYPE: DNA
<213> ORGANISM: Homo sapiens

<400> SEQUENCE: 8
ggttacgcgt caagattctg a                                              21

<210> SEQ ID NO 9
<211> LENGTH: 20
<212> TYPE: DNA
<213> ORGANISM: Homo sapiens

<400> SEQUENCE: 9
agactttcgg aacagaggca                                                20

<210> SEQ ID NO 10
<211> LENGTH: 22
<212> TYPE: DNA
<213> ORGANISM: Homo sapiens

<400> SEQUENCE: 10 atcttttttcc aggtcaacat ca                                            22

<210> SEQ ID NO 11
<211> LENGTH: 23
<212> TYPE: DNA
<213> ORGANISM: Homo sapiens

<400> SEQUENCE: 11
cattctattc atttcagtgg aca                                            23

<210> SEQ ID NO 12
<211> LENGTH: 22
<212> TYPE: DNA
<213> ORGANISM: Homo sapiens

<400> SEQUENCE: 12
gagatgtaga ggctggagaa ct                                             22

<210> SEQ ID NO 13
<211> LENGTH: 19
<212> TYPE: PRT
<213> ORGANISM: Bovine

<400> SEQUENCE: 13

Met Met Ser Phe Val Ser Leu Leu Leu Val Gly Ile Leu Phe His
 1               5                  10                  15

Ala Thr Glu Ala

<210> SEQ ID NO 14
<211> LENGTH: 15
<212> TYPE: PRT
<213> ORGANISM: Bovine

<400> SEQUENCE: 14

Met Lys Leu Leu Ile Leu Thr Cys Leu Val Ala Val Ala Ala Arg
 1               5                  10                  15

<210> SEQ ID NO 15
<211> LENGTH: 1448
<212> TYPE: PRT
```

<213> ORGANISM: Artificial
<220> FEATURE:
<223> OTHER INFORMATION: Bovine-Homo sapiens fusion protein

<400> SEQUENCE: 15

```
Met Lys Leu Leu Ile Leu Thr Cys Leu Val Ala Val Ala Ala Arg Leu
                 5                  10                  15

Thr Ala Thr Arg Arg Tyr Tyr Leu Gly Ala Val Glu Leu Ser
             20                  25                  30

Trp Asp Tyr Met Gln Ser Asp Leu Gly Glu Leu Pro Val Asp Ala Arg
                 35                  40                  45

Phe Pro Pro Arg Val Pro Lys Ser Phe Pro Phe Asn Thr Ser Val Val
             50                  55                  60

Tyr Lys Lys Thr Leu Phe Val Glu Phe Thr Asp His Leu Phe Asn Ile
             65                  70                  75

Ala Lys Pro Arg Pro Pro Trp Met Gly Leu Leu Gly Pro Thr Ile Gln
             80                  85                  90

Ala Glu Val Tyr Asp Thr Val Val Ile Thr Leu Lys Asn Met Ala Ser
 95                 100                 105                 110

His Pro Val Ser Leu His Ala Val Gly Val Ser Tyr Trp Lys Ala Ser
                115                 120                 125

Glu Gly Ala Glu Tyr Asp Asp Gln Thr Ser Gln Arg Glu Lys Glu Asp
                130                 135                 140

Asp Lys Val Phe Pro Gly Gly Ser His Thr Tyr Val Trp Gln Val Leu
             145                 150                 155

Lys Glu Asn Gly Pro Met Ala Ser Asp Pro Leu Cys Leu Thr Tyr Ser
 160                 165                 170

Tyr Leu Ser His Val Asp Leu Val Lys Asp Leu Asn Ser Gly Leu Ile
175                 180                 185                 190

Gly Ala Leu Leu Val Cys Arg Glu Gly Ser Leu Ala Lys Glu Lys Thr
                195                 200                 205

Gln Thr Leu His Lys Phe Ile Leu Leu Phe Ala Val Phe Asp Glu Gly
             210                 215                 220

Lys Ser Trp His Ser Glu Thr Lys Asn Ser Leu Met Gln Asp Arg Asp
             225                 230                 235

Ala Ala Ser Ala Arg Ala Trp Pro Lys Met His Thr Val Asn Gly Tyr
 240                 245                 250

Val Asn Arg Ser Leu Pro Gly Leu Ile Gly Cys His Arg Lys Ser Val
255                 260                 265                 270

Tyr Trp His Val Ile Gly Met Gly Thr Thr Pro Glu Val His Ser Ile
                275                 280                 285

Phe Leu Glu Gly His Thr Phe Leu Val Arg Asn His Arg Gln Ala Ser
             290                 295                 300

Leu Glu Ile Ser Pro Ile Thr Phe Leu Thr Ala Gln Thr Leu Leu Met
             305                 310                 315

Asp Leu Gly Gln Phe Leu Leu Phe Cys His Ile Ser Ser His Gln His
 320                 325                 330

Asp Gly Met Glu Ala Tyr Val Lys Val Asp Ser Cys Pro Glu Glu Pro
 335                 340                 345                 350

Gln Leu Arg Met Lys Asn Asn Glu Glu Ala Glu Asp Tyr Asp Asp Asp
                355                 360                 365

Leu Thr Asp Ser Glu Met Asp Val Val Arg Phe Asp Asp Asn Ser
             370                 375                 380

Pro Ser Phe Ile Gln Ile Arg Ser Val Ala Lys Lys His Pro Lys Thr
```

-continued

```
            385                 390                 395
Trp Val His Tyr Ile Ala Ala Glu Glu Asp Trp Asp Tyr Ala Pro
    400                 405                 410
Leu Val Leu Ala Pro Asp Asp Arg Ser Tyr Lys Ser Gln Tyr Leu Asn
415                 420                 425                 430
Asn Gly Pro Gln Arg Ile Gly Arg Lys Tyr Lys Lys Val Arg Phe Met
                435                 440                 445
Ala Tyr Thr Asp Glu Thr Phe Lys Thr Arg Glu Ala Ile Gln His Glu
            450                 455                 460
Ser Gly Ile Leu Gly Pro Leu Leu Tyr Gly Glu Val Gly Asp Thr Leu
                465                 470                 475
Leu Ile Ile Phe Lys Asn Gln Ala Ser Arg Pro Tyr Asn Ile Tyr Pro
    480                 485                 490
His Gly Ile Thr Asp Val Arg Pro Leu Tyr Ser Arg Arg Leu Pro Lys
495                 500                 505                 510
Gly Val Lys His Leu Lys Asp Phe Pro Ile Leu Pro Gly Glu Ile Phe
                515                 520                 525
Lys Tyr Lys Trp Thr Val Thr Val Glu Asp Gly Pro Thr Lys Ser Asp
            530                 535                 540
Pro Arg Cys Leu Thr Arg Tyr Tyr Ser Ser Phe Val Asn Met Glu Arg
    545                 550                 555
Asp Leu Ala Ser Gly Leu Ile Gly Pro Leu Leu Ile Cys Tyr Lys Glu
    560                 565                 570
Ser Val Asp Gln Arg Gly Asn Gln Ile Met Ser Asp Lys Arg Asn Val
575                 580                 585                 590
Ile Leu Phe Ser Val Phe Asp Glu Asn Arg Ser Trp Tyr Leu Thr Glu
                595                 600                 605
Asn Ile Gln Arg Phe Leu Pro Asn Pro Ala Gly Val Gln Leu Glu Asp
            610                 615                 620
Pro Glu Phe Gln Ala Ser Asn Ile Met His Ser Ile Asn Gly Tyr Val
    625                 630                 635
Phe Asp Ser Leu Gln Leu Ser Val Cys Leu His Glu Val Ala Tyr Trp
640                 645                 650
Tyr Ile Leu Ser Ile Gly Ala Gln Thr Asp Phe Leu Ser Val Phe Phe
655                 660                 665                 670
Ser Gly Tyr Thr Phe Lys His Lys Met Val Tyr Glu Asp Thr Leu Thr
                675                 680                 685
Leu Phe Pro Phe Ser Gly Glu Thr Val Phe Met Ser Met Glu Asn Pro
            690                 695                 700
Gly Leu Trp Ile Leu Gly Cys His Asn Ser Asp Phe Arg Asn Arg Gly
    705                 710                 715
Met Thr Ala Leu Leu Lys Val Ser Ser Cys Asp Lys Asn Thr Gly Asp
    720                 725                 730
Tyr Tyr Glu Asp Ser Tyr Glu Asp Ile Ser Ala Tyr Leu Leu Ser Lys
735                 740                 745                 750
Asn Asn Ala Ile Glu Pro Arg Ser Leu Lys Arg His Gln Arg Glu Ile
                755                 760                 765
Thr Arg Thr Thr Leu Gln Ser Asp Gln Glu Glu Ile Asp Tyr Asp Asp
            770                 775                 780
Thr Ile Ser Val Glu Met Lys Lys Glu Asp Phe Asp Ile Tyr Asp Glu
                785                 790                 795
Asp Glu Asn Gln Ser Pro Arg Ser Phe Gln Lys Lys Thr Arg His Tyr
800                 805                 810
```

```
Phe Ile Ala Ala Val Glu Arg Leu Trp Asp Tyr Gly Met Ser Ser Ser
815                 820                 825                 830

Pro His Val Leu Arg Asn Arg Ala Gln Ser Gly Ser Val Pro Gln Phe
                835                 840                 845

Lys Lys Val Val Phe Gln Glu Phe Thr Asp Gly Ser Phe Thr Gln Pro
            850                 855                 860

Leu Tyr Arg Gly Glu Leu Asn Glu His Leu Gly Leu Leu Gly Pro Tyr
        865                 870                 875

Ile Arg Ala Glu Val Glu Asp Asn Ile Met Val Thr Phe Arg Asn Gln
    880                 885                 890

Ala Ser Arg Pro Tyr Ser Phe Tyr Ser Ser Leu Ile Ser Tyr Glu Glu
895                 900                 905                 910

Asp Gln Arg Gln Gly Ala Glu Pro Arg Lys Asn Phe Val Lys Pro Asn
                915                 920                 925

Glu Thr Lys Thr Tyr Phe Trp Lys Val Gln His His Met Ala Pro Thr
            930                 935                 940

Lys Asp Glu Phe Asp Cys Lys Ala Trp Ala Tyr Phe Ser Asp Val Asp
        945                 950                 955

Leu Glu Lys Asp Val His Ser Gly Leu Ile Gly Pro Leu Leu Val Cys
    960                 965                 970

His Thr Asn Thr Leu Asn Pro Ala His Gly Arg Gln Val Thr Val Gln
975                 980                 985                 990

Glu Phe Ala Leu Phe Phe Thr Ile Phe Asp Glu Thr Lys Ser Trp Tyr
                995                 1000                1005

Phe Thr Glu Asn Met Glu Arg Asn Cys Arg Ala Pro Cys Asn Ile Gln
            1010                1015                1020

Met Glu Asp Pro Thr Phe Lys Glu Asn Tyr Arg Phe His Ala Ile Asn
        1025                1030                1035

Gly Tyr Ile Met Asp Thr Leu Pro Gly Leu Val Met Ala Gln Asp Gln
    1040                1045                1050

Arg Ile Arg Trp Tyr Leu Leu Ser Met Gly Ser Asn Glu Asn Ile His
1055                1060                1065                1070

Ser Ile His Phe Ser Gly His Val Phe Thr Val Arg Lys Lys Glu Glu
                1075                1080                1085

Tyr Lys Met Ala Leu Tyr Asn Leu Tyr Pro Gly Val Phe Glu Thr Val
            1090                1095                1100

Glu Met Leu Pro Ser Lys Ala Gly Ile Trp Arg Val Glu Cys Leu Ile
        1105                1110                1115

Gly Glu His Leu His Ala Gly Met Ser Thr Leu Phe Leu Val Tyr Ser
    1120                1125                1130

Asn Lys Cys Gln Thr Pro Leu Gly Met Ala Ser Gly His Ile Arg Asp
1135                1140                1145                1150

Phe Gln Ile Thr Ala Ser Gly Gln Tyr Gly Gln Trp Ala Pro Lys Leu
                1155                1160                1165

Ala Arg Leu His Tyr Ser Gly Ser Ile Asn Ala Trp Ser Thr Lys Glu
            1170                1175                1180

Pro Phe Ser Trp Ile Lys Val Asp Leu Leu Ala Pro Met Ile Ile His
        1185                1190                1195

Gly Ile Lys Thr Gln Gly Ala Arg Gln Lys Phe Ser Ser Leu Tyr Ile
    1200                1205                1210

Ser Gln Phe Ile Ile Met Tyr Ser Leu Asp Gly Lys Lys Trp Gln Thr
1215                1220                1225                1230
```

-continued

```
Tyr Arg Gly Asn Ser Thr Gly Thr Leu Met Val Phe Phe Gly Asn Val
                1235            1240            1245

Asp Ser Ser Gly Ile Lys His Asn Ile Phe Asn Pro Pro Ile Ile Ala
                1250            1255            1260

Arg Tyr Ile Arg Leu His Pro Thr His Tyr Ser Ile Arg Ser Thr Leu
                1265            1270            1275

Arg Met Glu Leu Met Gly Cys Asp Leu Asn Ser Cys Ser Met Pro Leu
                1280            1285            1290

Gly Met Glu Ser Lys Ala Ile Ser Asp Ala Gln Ile Thr Ala Ser Ser
1295            1300            1305            1310

Tyr Phe Thr Asn Met Phe Ala Thr Trp Ser Pro Ser Lys Ala Arg Leu
                1315            1320            1325

His Leu Gln Gly Arg Ser Asn Ala Trp Arg Pro Gln Val Asn Asn Pro
                1330            1335            1340

Lys Glu Trp Leu Gln Val Asp Phe Gln Lys Thr Met Lys Val Thr Gly
                1345            1350            1355

Val Thr Thr Gln Gly Val Lys Ser Leu Leu Thr Ser Met Tyr Val Lys
            1360            1365            1370

Glu Phe Leu Ile Ser Ser Ser Gln Asp Gly His Gln Trp Thr Leu Phe
1375            1380            1385            1390

Phe Gln Asn Gly Lys Val Lys Val Phe Gln Gly Asn Gln Asp Ser Phe
                1395            1400            1405

Thr Pro Val Val Asn Ser Leu Asp Pro Pro Leu Leu Thr Arg Tyr Leu
                1410            1415            1420

Arg Ile His Pro Gln Ser Trp Val His Gln Ile Ala Leu Arg Met Glu
                1425            1430            1435

Val Leu Gly Cys Glu Ala Gln Asp Leu Tyr
            1440            1445
```

TRANSGENIC MAMMAL SECRETING B-DOMAIN DELETED HUMAN FVII IN ITS MILK

BACKGROUND OF THE INVENTION

1. Field of the Invention

The present invention discloses a method for producing biologically active recombinant proteins in the milk of transgenic animals, characterized in which intact human clotting factor VIII gene and B-domain deleted recombinant factor VIII gene are transferred into the mammal by gene microinjection and embryonic implantation to obtain expression and secretion in the milk of transgenic animals and their offsprings.

2. Description of the Prior Art

Hemophilia is the most common human bleeding disorder and affects approximately one in 5,000 males, causing lifelong, repeated, and potentially life-threatening hemorrhagic episodes. It results from a deficiency in functional blood coagulation factors, either in a serine protease called Factor IX (hemophilia B) or in its cofactor Factor VIII (hemophilia A). Because hemophilia is caused by defects in single X-linked genes that encode circulating plasma proteins, the development of therapeutic strategies has focused on finding ways to replace the defective or deficient proteins.

Human FVIII is synthesized primarily in the liver and secreted into the circulation at low plasma concentration, approximately 100-200 ng/ml. Analysis of the cloned cDNA for human FVIII (Gitschier et al., 1984, Nature 312: 326-330; Toole et al., 1984, Nature 312: 342-347.) has provided more information about its gene and protein structure. The full length FVIII cDNA contains an open reading frame coding for a polypeptide of 2351 amino acids. This primary translation product contains a 19 a.a. signal peptides and six homologous domains in the order A1-A2-B-A3-C1-C2 (Vehar et al., 1984, Nature 312: 337-342.). The 256-kDa precursor protein is proteolytically processed intracellularly to a metal ion-linked heterodimer of a 90- to 200-kDa heavy chain (A1-A2-B) and an 80-kDa light chain (A3-C1-C2), which circulates in the plasma bound to the von Willebrand factor (vWF).

For the past two decades hemophiliacs have been treated with whole plasma, and more recently with highly purified FVIII concentrates prepared from plasma. Higher concentrates purity allows the administration of effective doses at lower volumes to patients. This therapy is effective in controlling bleeding episodes, however, hemophiliacs may suffer from other complications, compromised by the discovery that these products were transmitting human viruses such as the hepatitis B virus and human immuno-deficiency virus (HIV) to patients, many of them later developed diseases (Hoyer, 1993, Methods Enzymol. 222: 169-176).

Since then, plasma screening and viral inactivation procedures have greatly improved the safety of these products, although the potential for transmitting diseases such as Creutzfeldt-Jakob disease must be considered and has led to sporadic shortages in these plasma products. Nonetheless, when non-blood source products derived from recombinant DNA biotechnology became available, further reducing the viral risk, they were quickly embraced by caregivers and patients, despite their higher cost (Pipe and Kaufman, 2000, Nature Biotech. 18: 264-265). One of the challenges created by the biotechnology revolution is the development of methods for the economical production of highly purified proteins in large scales. Recent developments indicate that manipulating milk composition using transgenesis has focused mainly on the mammary gland as a bioreactor to produce pharmaceuticals.

SUMMARY OF THE INVENTION

The ability to modify animal genomes through microinjection technology has offered new alternatives for the manufacture of recombinant proteins. Targeting the production of human recombinant protein pharmaceuticals in the milk of transgenic animals solved many problems associated with either microbial or animal cell expression systems. Bacteria often improperly fold complex proteins, introducing more involved and expensive processes. Both bacteria and yeast lack adequate post-translational modification. Bioreactors for cell cultures require high capital expenditures, use large volumes of expensive culture media, and often suffer from relatively low yields.

To express a recombinant protein in the milk of a transgenic animal, expression vectors containing a gene encoding the protein of interest fused to milk specific regulatory promoter elements are generally introduced by microinjection into a pronuclear-stage embryo, or alternatively transfecting the expression vector into a cell line suitable for somatic cell nuclear transfer. Most of this work has been carried out with: the ovine β-lactoglobulin, rodent (mouse, rat and rabbit) whey acid protein (WAP) genes, bovine α-lactalbumin and a-s1-casein genes, as well as the caprine β-gene.

Several blood proteins, hormones, and enzymes have been synthesized in transgenic animals. Of these, human FVIII is probably the largest and most complex protein to be expressed. Analysis of the cloned cDNA for human FVIII has provided more information about its gene and protein structure. The full length FVIII cDNA contains an open reading frame coding for a large polypeptide of 2351 amino acids. The 256-kDa precursor hFVIII protein is proteolytically processed intracellularly to a metal ion-linked hetero-dimer of a 90- to 200-kDa heavy chain (A1-A2-B) and an 80-kDa light chain (A3-C1-C2), which circulates in the plasma bound to the von Willebrand factor (vWF). The B-domain, is encoded by a single large exon and is highly glycosylated, harboring 19 of the 25 N-linked glycosylation sites. The B-domain is released upon co-factor activation, so it is not necessary for clotting function.

According to the regulatory sequences employed, variable levels of expression for the recombinant human FVIII were observed. For example, using a construct containing 2.2-kb ovine β-lactoglobulin 5'-flanking sequences to drive the FVIII cDNA with the introns of the murine metallothionein I (β-Lac/hFVIII-MtI), only extremely low level (4-6 ng/ml) of expression was observed in transgenic sheep (Niemann et al., 1999. Transgenic Res 8: 237-247). Whereas the hFVIII cDNA, under the control of the 2.5-kb mouse WAP promoter, was shown to secrete up to 2.7 µg/ml in transgenic pig milk (Paleyanda et al., 1997. Nature Biotech 15: 971-975).

In this invention, we describe a novel recombination of promoter, leader sequence, coding sequences and poly A tail signaling sequence as a expression cassette to generate of transgenic animals expressing the fusion gene in the mammary gland and the presence of recombinant FVIII protein ranged from 7 to 50 µg/ml with over 35- to 200-fold higher than in normal human plasma, with temporal and spatial expression profiles for clotting active rFVIII in the milk of transgenic animals in different stages of lactation.

BRIEF DESCRIPTION OF THE DRAWINGS

The file of this Patent contains at least one Drawing Figure executed in color. Copies of the Patent with color Drawings will be provided by the Patent and Trademark Office upon request and payment of the necessary fee.

FIG. 1A The structure of αLA-hFVIII-bGHpA fusion genes are shown and a pair of primer sets for PCR screening and a 1.8-kb hFVIII kpnI-fragment as probe were designed franking the 5'-end and 3'-end of hFVIII cDNA, respectively.

FIG. 1B Rapid screening positive transgenic mice founders by PCR amplification. NC represented a normal mouse DNA as a negative control.

FIG. 1C Screening of positive transgenic goat founders and F1 offspring by PCR amplification. NC represented a normal non-transgenic goat DNA as a negative control.

FIG. 1D Southern blot analysis of the integration patterns of transgene DNA in transgenic animals. Genomic DNA extracted from different founders of transgenic mice tails or transgenic goats' ear tissues were digested with BamHI and subjected to probe hybridization.

FIG. 2A The relative positions of sample loading for standard controls and transgenic founders. The standards were made with calculated hFVIII plasmid DNA, 0.5 to 20 copy numbers, mixed with 10 ug of normal mouse genomic DNA. The lanes of transgenic founders were also slotted with 10 ug of undigested genomic DNA. A kpnI fragment of hFVIII cDNA was used as a hybridization probe. Hybridization and wash was performed in high stringency condition (70° C.) to avoid cross-hybridization. Result is shown in FIG. 2B.

FIG. 3A The structure of αLA-CN-hFVIII(ΔB)-bGHpA fusion genes are shown and two pairs of primer sets for PCR screening and a 1.8-kb hFVIII kpnI-fragment as probe were designed franking the 5'-end, B-domain flanking region and 3'-end of hFVIII cDNA, respectively.

FIG. 3B DNA sequencing confirmed the in-frame creation of the N-terminal αS1-casein signal peptide sequence and the 19-aa leader pepteide-removed hFVIII sequence.

FIG. 3C DNA sequencing confirmed the in-frame creation of B-domain deletion between hFVIII A-domain (A1-A2) and hFVIII C-domain (A3-C1-C2).

FIG. 4A The structure of αLA-CN-hFVIII(ΔB)-bGHpA fusion genes are shown and two pairs of primer sets for PCR screening, 273-bp for the 5'-end franking region and 751-bp for the B-domain flanking region, respectively. It also shows the genomic digested enzymes and predicted patterns in Southern blot assay.

FIG. 4B Rapid screening positive transgenic founders by PCR amplification. NC represented a normal mouse DNA as a negative control. PC represented a hFVIII(ΔB) plasmid DNA as a positive control.

FIG. 4C Southern blot hybridization analysis of transgenic goat (Tg-3431) harboring B-domain-deleted hFVIII fusion gene. Normal and transgenic goat genomic DNAs were digested with HindIII, PvuII, and XbaI, individually. Arrowheads represented the off-size bands in transgenic goat genome.

FIG. 6A Tissue-specific expression of αLA-FVIII transgene by RT-PCR detection. Tissue was removed from lactating mice at 7 days post partum. RNA was isolated from lactating transgenic mouse mammary gland (Ma), heart (H), liver (L), lung (Lu), muscle (M), brain (B), prancreas (P), and in male transgenic mouse mammary fat pad (F). A b-actin primer set was used as internal control.

FIG. 6B Stage-specific expression of αLA-FVIII transgene during pre-partum (D-3), lactation (D1 to D22), and weaning (D29 to D36). A glyceraldehyde-3-phosphate dehydrogenase (GAPDH) primer set was used as an internal control. The ratios of hFVIII/GAPDH band intensities were plotted by densitometer with computer analysis (Bio-Rad video densitomer, model 620).

FIG. 7A The secretion of rFVIII protein in milks was collected, 10- to 20-fold diluted and subjected to western blotting with rabbit anti-hFVIII polyclonal antiserum. Lane 1 contained the milk protein harvested from non-transgenic mice during lactating stage as a negative control and lane 2 contained HPLC-purified hFVIII heavy chain (200-kDa) as a positive control. The orders for D7, D12, D17, and D22 represented the milk proteins harvested from various lactating stages of transgenic mice.

FIG. 7B Western blotting analysis of rFVIII light chain protein with mouse anti-hFVIII monoclonal antibody D2. Lane 1 contained the milk protein harvested from non-transgenic mice during lactating stage as a negative control and lane 2 contained the HPLC-purified hFVIII light chain (80-kDa) as a positive control.

FIG. 9A Human FVIII dilutions equivalent to a 1% to 50% dilution of normal plasma (NPP) were prepared in 50 mM imidazole buffer.

FIG. 9B NPP standard curve was performed using aPTT clotting assay.

FIG. 9C Control and transgenic goat milks diluted in 50%, 20%, and 10% were incubated in duplicate at 37° C. in hFVIII-deficient plasma, followed by the automated addition of aPTT reagent. The clot time, in seconds, was recorded on an ST2 Coagulometer (Stago).

DETAILED DESCRIPTION OF THE INVENTION

Figure 1A:
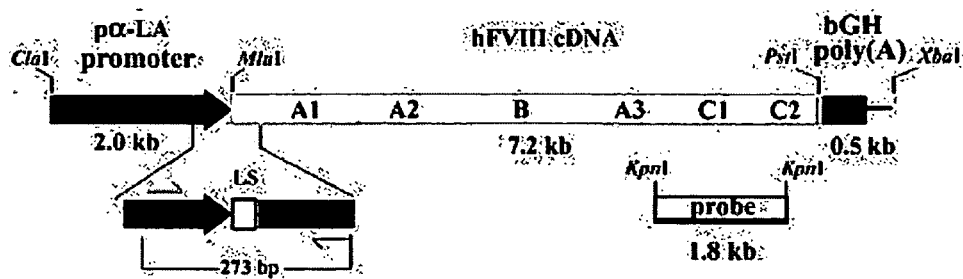
FIG. 1A~1D shows a schematic map of full-length hFVIII transgene construction and detection of transgene integrated patterns in transgenic animals.

The invention relates to a non-human transgenic animal that produces therapeutical recombinant hFVIII in the milk of the non-human transgenic animal for treating hemophilia patients.

Using mammary gland-specific promoters, a wide range of proteins of bio-pharmaceutical interest have been expressed in rodents, pigs, and dairy animals (Echeland, 1996, Current Opinion in Biotechnology 7: 536; Houdebine et al., 2000, Transgenic Research 9:505). An expression vector, comprising a gene encoding the target protein of interest fused to a milk promoter gene, is introduced by microinjection into the pronucleus of a one-cell embryo. Upon germ line integration and expression, the transgene acquires a dominant Mendelian genetic characteristic that is inherited by the progeny of the founder animal. Mammary epithelial cells of the non-human transgenic animal have the capacity to carry out complex protein synthesis with a variety of posttranslational modifications and folding.

Milk Specific Promoters

A variety of transcriptional promoters that preferentially activate transcription in mammary epithelial cells are available. These include the promoters that control the genes encoding milk proteins such as caseins (αS1-, αS2-, β-, γ-, and κ-casein), beta-lactoglobulin (Clark et al., 1989, Bio/Technology 7: 487-492), whey acid protein (Gordon et al., 1987, Bio/Technology 5: 1183-1187), and alpha-lactalbumin (Soulier et al., 1992, FEBS Letters 297: 13). Casein promoters may be derived from the alpha, beta, gamma or kappa casein genes of any mammalian species; a preferred promoter is derived from the goat beta casein gene (DiTullio, 1992, Bio/Technology 10:74-77).

The DNA sequences of many these promoters are available, e.g., in GenBank and in scientific publications such as 1) rat alpha-lactalbumin (Richards et al., 1981, J. Biol. Chem. 256: 526-532); 2) rat WAP (Campbell et al., 1984, Nucleic Acids Res. 12: 8685-8697); 3) rat alpha-casein (Jones et al., 1985, J. Biol. Chem. 260: 7042-7050); 4) rat alpha-casein (Lee and Rosen, 1983, J. Biol. Chem. 258: 10794-10804); 5) human alpha-lactalbumin (Hall, 1987, Biochem. J. 242: 735-742); 6) bovine alpha-S1 casein (Stewart, 1984, Nucleic Acids Res. 12: 389); 7) bovine alpha-casein (Gorodetsky et al., 1988, Gene 66: 87-96); 8) bovine alpha-casein (Alexander et al., 1988, Eur. J. Biochem. 178: 395-401); 9) bovine alpha-S2 casein (Brignon et al., 1977, FEBS Letters 188: 48-55); 10) bovine alpha-lactoglobulin (Jamieson et al., 1987, Gene 61: 85-90; Alexander et al., 1989, Nucleic Acids Res. 17: 6739). For additional regulatory control or stringency, other regulatory sequences such as adjacent sequences, can be obtained from these genes or from homologous genes of other mammals using these promoter sequence as probes to screen genomic libraries.

Signal Peptide Sequences

The recombinant gene construction can also include signal sequences, particularly signal peptide sequences of a milk specific gene. To achieve optimal secretion of foreign protein by the mammary gland, the milk-specific signal peptide sequence, such as a secretional signal sequence which naturally occurs with the selected milk-specific promoter, can be used in the construct. For example, signal sequences from genes coding for caseins, e.g., alpha, beta, gamma or kappa caseins, beta lactoglobulin, whey acid protein, and lactalbumin can be used.

Transgenesis Constructions

A 2.0-kb promoter sequence of bovine alpha-lactalbumin (αLA) was generated by PCR amplification using a genomic DNA from high milk-producing Holstein cow, which obtained from National Taiwan University Farm, as the template. This PCR product contains an entire αLA promoter and a 19-aa leader sequence encoded by a DNA sequence of SEQ ID NO: 1 or replacement with a 15-aa bovine αS1-casein signal peptide sequence encoded by another DNA sequence of SEQ ID NO: 2, as well as a restriction enzyme, (HpaI) cloning site created downstream of the DNA sequence of SEQ ID NO: 1 or SEQ ID NO: 2. The promoter and signal peptide sequences were then subsequently inserted into the pCR3 vector (Invitrogene, San Diego, Calif.).

For the full-length hFVIII construction, a 7.0-kb resultant plasmid containing αLA promoter and its intact signal peptide sequence was double digested with MluI and PstI and treated with calf intestinal phosphatase (Boehringer Mannheim, Indianapolis, Ind.). The pCMV5/hFVIII plasmid containing the intact human FVIII coding sequence was also double digested with MluI and PstI. The in-frame sequence from the αLA leader peptide through the hFVIII junction was determined using the Dye Terminator sequencing system (Applied Biosystems Inc., Foster, Calif.). The 9.7-kb transgene consisting of 2.0-kb bovine αLA promoter, 7.2-kb hFVIII cDNA, and 0.5-kb bovine GH gene polyadenosine signal sequence was separated from plasmid pCR-.alpha.LA/hFVIII-5 using ClaI and XbaI digestion and purified by ultra-centrifugation twice through a $CsCL_2$ gradient before microinjection.

For the B domain-deleted hFVIII construction, the 7.0-kb resultant plasmid containing αLA promoter and αS1-casein signal peptide sequence was double digested with HpaI and XhoI and treated with calf intestinal phosphatase (Boehringer Mannheim, Indianapolis, Ind.). The pCMV5/hFVIII plasmid containing the intact human FVIII coding sequence was used as a template to generate a 2233-bp rhFVIII A-domain fragment by degenerate PCR, using a pair of primers phFVIII-HpaI(+): 5'-GGT TAA CTG CCA CCA GAA GAT A-3' (SEQ ID NO: 3) and phFVIII-741aa(−): 5'-AAG CTT CTT GGT TCA ATG GC-3' (SEQ ID NO: 4), and a 2085-bp rhFVIII C-domain fragment amplified by a pair of primers phFVIII-1643aa(+): 5'-AAG CTT GAA ACG CCA TCA ACG GGA A-3' (SEQ ID NO: 5) and phFVIII-XhoI(−): 5'-CTC GAG CCT CAG TAG AGG TCC TGT-3' (SEQ ID NO:6), respectively. A-domain segment, C-domain segment and pCR3-αLA vector of equal molar ratio were co-ligated and transformed into host competent cells. The in-frame sequence from the αS1-casein leader peptide through the hFVIII junction was determined using the Dye Terminator sequencing system (Applied Biosystems Inc., Foster, Calif.). The 6.8-kb transgene consisting of 2.0-kb bovine αLA promoter and αS1-casein leader sequence, 4.3-kb hFVIII cDNA, and 0.5-kb bovine GH gene polyadenosine signal sequence was separated from plasmid pCR-αLA/hFVIII(ΔB) using ClaI and XbaI digestion and purified-by ultra-centrifugation twice through a $CsCl_2$ gradient before microinjection.

Transgenic Animal Productions

The purified transgene was microinjected into the male pronuclei of fertilized eggs from superovulated female mice of the outbreed ICR strain and transferred to recipient pseudo-pregnant females as previously described (Chen et al., Transgenic Res 4: 52-59; 1995). For transgenic goat production, the pronuclear stage embryos were flushed from the donor goat's oviduct at the one and a half day after insemination by means of a surgical method. In order to obtain a larger number of embryos, every embryo-donating goat had been treated with endocrine to achieve superovulation. The superovulation treatment involves intramuscular administration of follicular stimulating hormone (FSH) to the embryo-donating goat twice a day with an interval of 12 hours for 4 consecutive days from the eighth day of the estrous cycle and the dosage was gradually decreased daily as 4-, 3-, 2-, and 1-mg, respectively. On the third day, the first dosage of FSH was co-administrated with 1000 iu human chorionic gonadotropin (HCG) which resulted in detection of estrogen 54 hours after two artificial inseminations (AI) were given with an interval of 12 hours. Then, at about one and a half days after conception, the one-cell stage goat embryos were collected with a sterile glass capillary tube via a surgical embryo flushing method. The collected embryo was transferred into another petri dish and rinsed more than ten times. Thereafter, the collected embryo was placed under a phase contrast microscope at 400× amplification for gene microinjection manipulation. After a transient in vitro culture, the healthly microinjected embryos were then transferred into recipient oviducts for further conception development.

Recombinant hFVIII Transgene Determination

The resulting pups were rapidly screened for the transgene by PCR amplification of tail or ear tissue DNA. PCR was performed using one set of primers, pαLA-124(+): 5'-CTC TCT TGT CAT CCT CTT CC-3' (SEQ ID NO: 7) and phFVIII-149(−): 5'-GGT TAC GCG TCA AGA TTC TGA-3' (SEQ ID NO: 8), which defined a 273-bp region spanning the αLA promoter, secretion signal sequence and hFVIII cDNA junctional sequence. For the B domain-deleted hFVIII transgene detection, additional primer pairs were designed, phFVIII-ACJ(+): 5'-AGA CTT TCG GAA CAG AGG CA-3' (SEQ ID NO: 9) and phFVIII-ACJ(−): 5'-ATC TTT TTC CAG GTC AAC ATC A-3' (SEQ ID NO: 10), which defined a 751-bp region flanking A-C recombinant junction. The positive PCR screening results for transgenic animals were further confirmed by Southern blot analysis. Ten micrograms of genomic DNA were individurally digested with BamHI, HindIII, PvuII, and XbaI restriction enzymes at 37° C. overnight, electrophoresed on a 0.8% agarose gel, and transferred to a Durose membrane (Stratagene, La Jolla, Calif.). A KpnI fragment of hFVIII-specific cDNA (1.8-kb) was used as a radioactive probe to hybridize the membrane. Blots were subjected to autoradiography for three days at −20° C.

Recombinant hFVIII RNA Expression in Transgenic Animals

The temporal and spatial expression of hFVIII RNA in transgenic animals was analyzed using a reverse transcription-polymerase chain reaction (RT-PCR). Total RNA from different tissues including the heart, liver, lung, muscle, mammary gland, brain, pancreas, and kidney of female transgenic mice during lactation periods (Day 1 to Day 28 post partum) was extracted using the acid guanidinium thiocyanate method (Chomczynski and Sacchi, 1987, Anal. Biochem. 162: 156-159). One microgram of total RNA was treated twice with 10 units of DNase I (Gibco BRL, Gaithersburg, Md.) and phenol-chloroform extract. RNA pellets were resuspended in 15 µl DEPC-water and then used to synthesize the first-strand cDNA with random primers and SuperScript reverse transcriptase (Gibco BRL, Gaithersburg, Md.) in a total volume of 25 ml. The reaction was carried out at 42° C. for 1 hr.

For further PCR amplification, an aliquot (1/10) of the RT product was adjusted to contain 0.1 µg of each primer and additional buffer was added for a total volume of 50 µl. PCR was performed for 30 cycles (94° C., 1 min; 55° C., 2 min; 72° C., 2 min). The primers used included a pair of hFVIII-specific primers, phFVIII-F2(+):5'-CAT TCT ATT CAT TTC AGT GGA CA-3' (SEQ ID NO: 11) and phFVIII-R2(−): 5'-GAG ATG TAG AGG CTG GAG AAC T-3' (SEQ ID NO: 12), and a pair of glyceraldehydes-3-phosphate dehydrogenase (GAPDH), as well as a pair of β-actin. Both β-actin and GAPDH are the universal transcripts in every cell and were used as the internal controls of RT-PCR.

Immunoblot Analysis of Transgenic Milk Proteins

Milk was collected from lactating females as previously described (Simons et al., 1987, Nature 328: 530-532) and analyzed using SDS-polyacrylamide gel electrophoresis (SDS-PAGE) (Cheng et al., 1998, Human Gene Therapy 9: 1995-2003). Ten- to twenty-fold dilutions of the collected milk, in 75 mM Tris-HCl buffer at pH 6.8, from different lactation periods were diluted in SDS-PAGE sample buffer with 5% 2-mercaptoethanol and electrophoresed on 7.5% gel. To estimate production levels, HPLC-purified recombinant hFVIII standard was diluted to 10 µg/ml in normal mouse milk and electrophoresed alongside the milk samples from the transgenic animals. Proteins were transferred from the gel to a PVDF membrane (NEN Life Science Products, Boston, Mass.). The protein blots were probed with primary antibodies binding to hFVIII at 2 to 10 µg/ml and washed with phosphate-buffered saline containing 0.1% Tween-20 (PBS-T). The protein blots were further reacted with horseradish peroxidase (HRP)-conjugated secondary antibodies at 0.2 mg/ml. The Polyclonal antibody C6 binds to the heavy chain of hFVIII and ranged from 80-200 kDa and the monoclonal antibody D2 binds to the light chain of hFVIII at 75-80 kDa. The blot was then developed with the chemiluminescent (ECL™) detection system (Amersham, UK) and exposed on a x-ray film. Band intensities were compared by densitometry.

Secretion of hFVIII protein from the milk of the transgenic animal was determined quantitatively with the enzyme-linked immunosorbent assay (ELISA) as previously described (Chen et al., 1993, J Virol 67: 2142-2148). Briefly, plates were coated with capture antibodies (ESH-5 and ESH-8, 500 ng each per well; American Diagnostics, Greenwich, Conn.) in carbonate buffer and incubated for 1 hour at 37° C. Plates were washed with 0.05% Tween-20 in phosphate-buffered saline (PBS) and blocked in 50 mM Tris (pH 7.2), 150 mM NaCl, 0.5% gelatin, and 0.05% Tween-20 for 2 hour at 37° C. Purified recombinant FVIII (Hyland, Baxter Healthcare, Calif.), prepared in blocking buffer with 1:50 normal murine milk, served as the standard. Samples and standards were incubated for 1 hour at 37° C. Detection antibody (rabbit anti-human FVIII 1:10,000 dilution) was added and allowed to react with hFVIII at 37° C. for 1 h. After non-specific binding of primary antibody was removed by four washes with PBS, a secondary antibody, goat anti-rabbit immunoglobulin antibody conjugated with horseradish peroxidase, was added (1:3,000 dilution) and incubated for another hour. The plates were washed again thoroughly with PBS, and 100 µl of substrate solution (2 mg of 0-phenylenediamine dissolve in 1 ml of 1M phosphate citrate plus 0.02% $H_2O_2$) was added for development. After 30 min, 100 µl of 1M $H_2SO_4$ was added immediately to stop the reaction and the colors were measured by optical density at 492 nm.

The Feature of α-Lactalbuimn Mammary Expression Cassette

Expression of rFVIII protein in the milk of transgenic animals driven by bovine α-lactalbuimn regulatory sequence seems more efficient than the other transgene constructions, which were controlled by bovine β-lactoglobulin promoter (Niemann et al., 1999, Transgenic Res 8: 237-247) as well as mouse WAP regulatory sequence (Paleyanda et al., 1997, Nature Biotech 15: 971-975). Expression of the bovine αLA gene has been shown to be the most lactation-specific of all bovine milk protein genes (Goodman and Schanbacher, 1991, Biochem Biophys Res Commun 180:75-84). Use of the αLA 19-aa secretory peptide (SEQ ID NO: 13) or αS1-casein 15-aa signal peptide (SEQ ID NO: 14) to lead the rFVIII protein secretion and the bGH polyadenosylation signal to stabilize the steady-state of hFVIII RNA molecules may also have contributed to our success. Several previous reports have demonstrated that mammary specific transgenes driven by αLA promoter have resulted in high levels of gene expression up to 3.7 mg/ml (Hochi et al., 1992, Mol Reprod Dev 33: 160-164; Soulier et al., 1992, Fed Eur Biol Soc Lett 297: 13-20; Maschio et al., 1991, Biochem J 275:459-465) in the milk of the transgenic animal. This characteristic of the bovine αLA gene makes its regulatory elements potentially useful as a mammary expression system in transgenic animals. In contrast to the caseins and β-lactoglobulin, the production of αLA mRNA increases suddenly at paturition, remains elevated during lactation, and drops sharply at dry-off and during involution. The rFVIII protein profile led by the αLA promoter and 19-aa secretion signal peptide or αS1-casein 15-aa signal peptide follows a similar trend. The lactation specificity of the regulatory regions used to control mammary expression in transgenic animals may be important when foreign proteins having biological activities are expressed since these proteins may exert their biological activities on the animals if they are secreted before tight junctions of mammary epithelial cells are formed.

The Feature of hFVIII Protein Expression

Clotting factor IX (FIX), adenosine deaminase (ADA), and other cDNAs were expressed at high levels from retroviral vectors in rat fibroblasts (Miller, 1992, Nature 357: 455-460; Palmer et al., 1991, Proc Natl Acad Sci USA 88: 1330-13334), whereas the FVIII cDNA was expressed at very low levels from these vectors in primary human fibroblast cells (Hoeben et al., 1990, J Biol Chem 265: 7318-7323; Lynch et al., 1993, Hum Gene Ther 4: 259-272). It has been found that FVIII RNA steady-state levels were reduced 100-fold from a FVIII retroviral vector compared to the same vector expressing other cDNAs, and FVIII vector titers were correspondingly reduced 100-fold compared to other vectors (Lynch et-al., 1993, Hum Gene Ther 4: 259-272). A large part of the inhibitory effect of the FVIII cDNA on expression from a retroviral vector has been localized to a 1.2-kb fragment, derived from the A2 and A3 domains, which decreased the steady-state RNA levels 100- to 200-fold and decreased vector titers 10-fold (Koeberl et al., 1995, Hum Gene Ther 6: 469-479). The mechanism by which the FVIII cDNA inhibitory sequence (INS) decreases RNA and protein expression from expression vectors remains to be established. Recently, experimental data provided ample evidence that the human FVIII cDNA contains elements that repress its own expression at the level of transcription (Hoeben et al., 1995, Blood 85: 2447-2454). Fallaux and coworkers (1996, Mol Cell Biol 16: 4264-4272) identified a 305-bp region derived from exons 9 to 11 that encodes a nuclear-matrix attachment region (MAR), also called the scaffold-attached region (SAR). Yeast MARs elements can play an important role in transcriptional silencing (Newlon and Theis, 1993, Transgenic Res 8: 237-247). B-domain-deleted hFVIII cDNA (BDD-hFVIII) is a 4.3 kb sized sequence that encodes a primary truncate polypeptide (hFVIIIΔB) of (SEQ ID NO: 15) not previously thought feasible for testing in transgenic animals.

The present invention is further depicted in the illustration of examples, but the descriptions made in the examples should not be construed as a limitation on the actual application of the present invention.

EXAMPLE 1

Figures 1B, 1C:
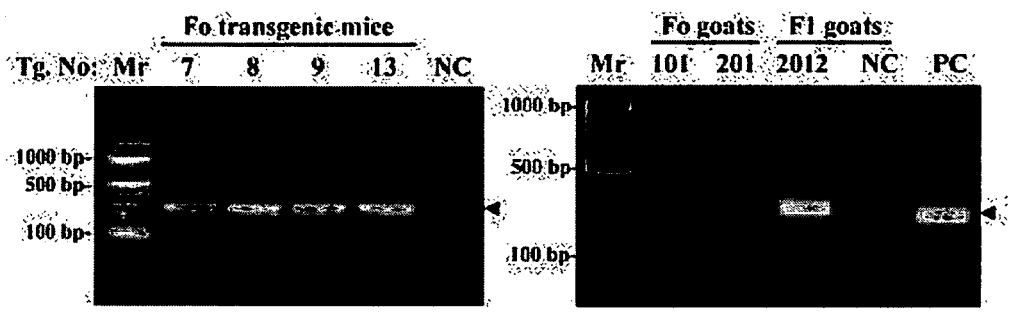
Figure 1D:
Figures 2A, 2B:
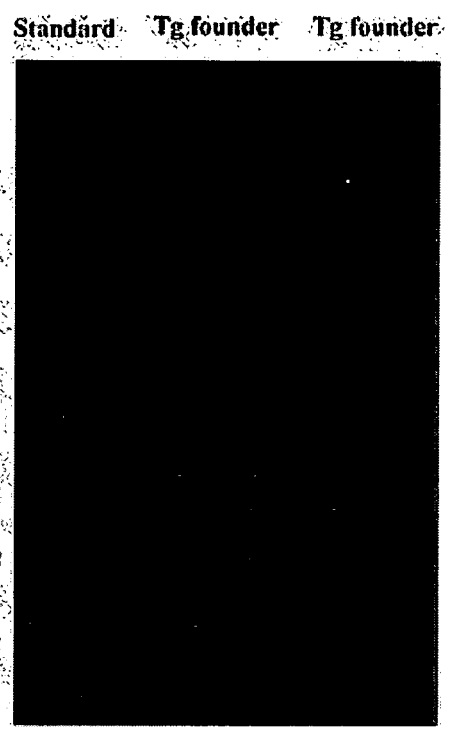
FIG. 2A~2B represents the determination of hFVIII transgene copy numbers in 17 transgenic founders using slot-blot hybridization.

Generations of Transgenic Mice, Pigs and Goats Carrying the Full-Length hFVIII Gene in Mammary-Specific Expression Cassette Out of 79 potential transgenic founder mice, 17 were identified as being transgenic by the PCR screening (FIG. 1B). Two transgenic founder goats carrying the full-length hFIII also have been identified by PCR screening (FIG. 1C) as well as two lines of transgenic pigs have been established. To quantify the transgene copy numbers and to understand the integration patterns of the foreign gene within the genome the transgenic animals, restriction enzyme BamHI was used to digest the genomic DNA, cut once within the transgene, and subjected to Southern blotting analysis. On hybridization using the 1.8-kb KpnI fragment of human-specific FVIII sequence as a probe (FIG. 1A), a 9.7-kb band representing monomeric transgene copies present in head-to-tail joining (H-T) tandem repeats was observed in all cases. A 4.6-kb hybridization band was observed in the blots of all transgenic mice present in tail-to-tail joining (T-T) inverted repeats (FIG. 1D). Different intensities of the hybridization signal were also observed indicating the presence of different transgene copy numbers in these mice. A slot-blot hybridization was further carried out for detailed quantification (FIG. 2A~and 2B) of the hybridization signal, which could be classified into three groups according to the copies of transgene integration. For low copy number (defined as 1-5 copies per cell), there were six transgenic lines including αLAF-7, -15, -33, -36, -43 and -54. Transgenic founders carrying middle copy number (10-20 copies per cell) were found in nine lines including αLAF-9, -13, -18, -27, -28, -29, -30, -38 and -39. In addition, there were two lines (αLAF-8 and -25) carrying high copy number (40-50 copies per cell) of hFVIII transgene in their genome. All of the transgenic mice harboring αLA-hFVIII DNAs presented two-to-three off-size bands (FIG. 1D) besides the predicted transgene junctions. These bands were probably rearranged transgene sequences, some of which were integration sites representing transgene-cellular junctions.

Breeding lines were established from all transgenic founder animals by crossing them with normal ICR mice, Alpine goats, or hybrid pigs. The multiple integrated copies of the transgene were found to be stably germ-line transmitted among twelve (7 females and 5 males) out of the 17 transgenic founders.

EXAMPLE 2

Figure 3A:
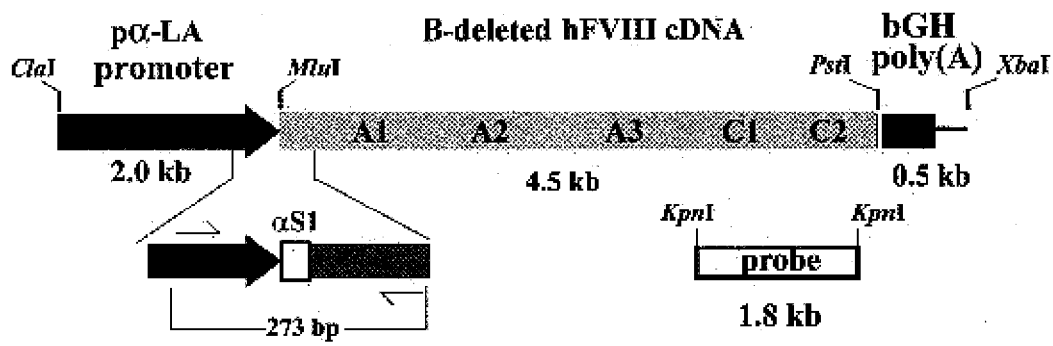
FIG. 3A~3C provides a schematic map of B-domain deleted hFVIII transgene construction and detection of transgene junctional sequences.
Figure 3B:
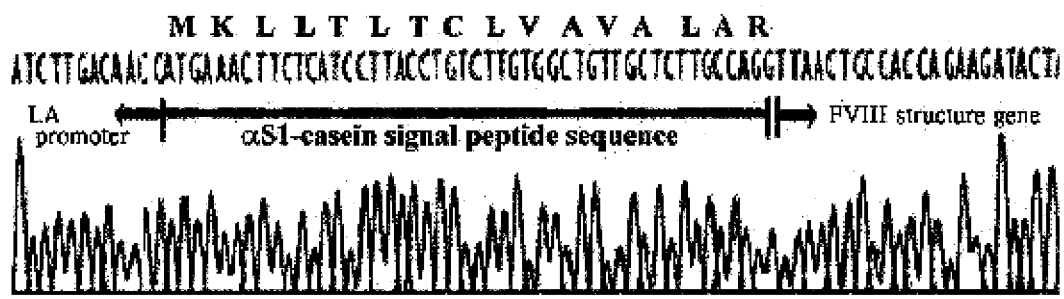

Generations of Transgenic Mice and Goats Carrying the B-Domain Deleted hFVIII Gene in Mammary-Specific Expression Cassette B-domain deleted hFVIII transgene construct driven by αLA promoter and αS1-casein secretary peptide sequence was shown in FIG. 3A. In N-terminal of rhFVIII polypeptide, a 15-aa αS1-casein signal peptide was added for leading newly synthesized rhFVIII secretion into mammary ductal cavity (FIG. 3B).

Figure 3C:
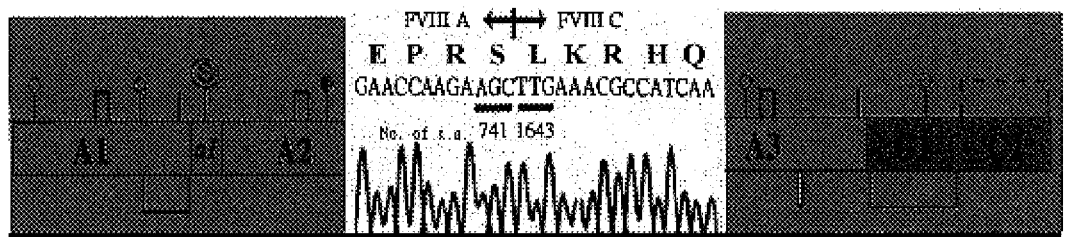

In the middle of rFVIII polypeptide, the A-domain (741-residue) has been created to join the C-domain (1643-residue) for completely deleting the B-domain segment (FIG. 3C).

Figure 4A:
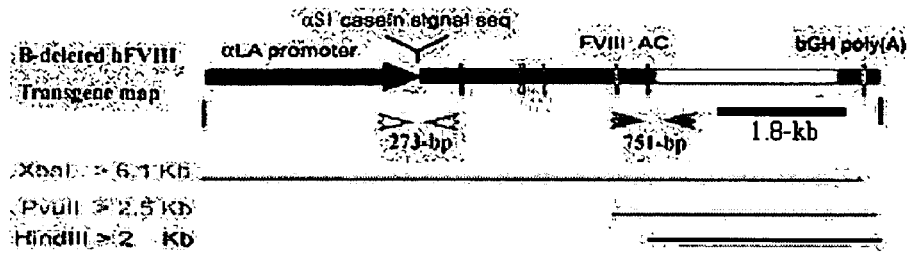
FIG. 4A~4C shows the analyzed data of B domain-deleted hFVIII transgenic animals.
Figure 4B:
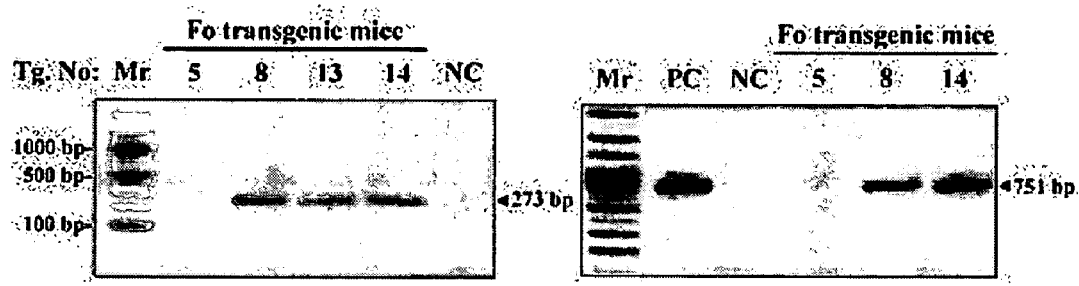
Figure 4C:
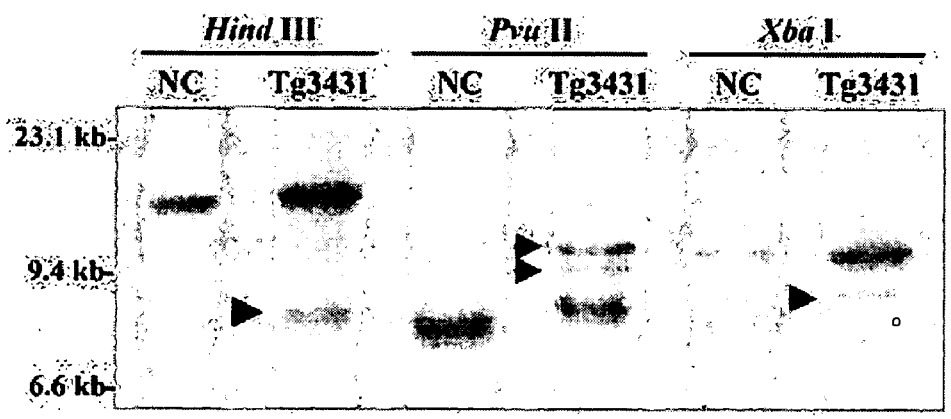

Out of 65 potential transgenic founder mice, 15 were identified as being transgenic by the two sets of primers, with one pair of primers located in the 5'-promoter junction, and the other pair of primers flanking the B-domain deletion region (FIG. 4A). The PCR screening was shown in FIG. 4B. To quantify the transgene copy numbers and to understand the integration patterns of the foreign gene within the genome of the transgenic mice, restriction enzyme HindIII, PvuII, and XbaI were used to digest the genomic DNA, cut once within the transgene, and subjected to Southern blotting analysis (FIG. 4C). The result showed that transgenic goat (Tg-3431) harboring B-domain-deleted hFVIII fusion gene clearly exhibited one to two off-size bands in their genome when compared with normal goat genome.

Figure 5:
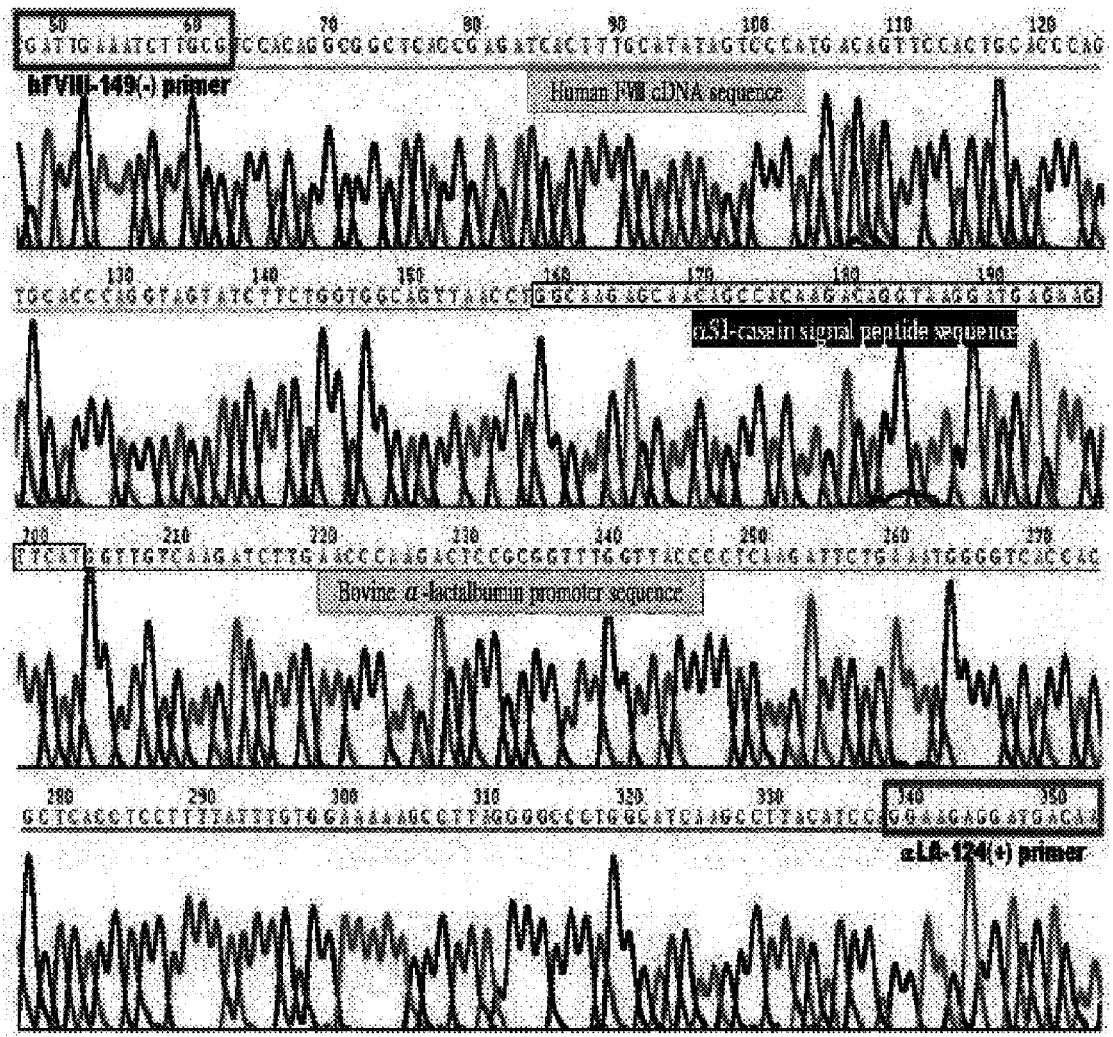
FIG. 5 confirms the germ-line transmission of transgenic animals carrying hFVIII(ΔB) exogenous DNA in their F1 generation by using PCR detection and direct PCR product sequencing. The sequencing result exhibited the intact transgenic hFVIII(ΔB) fragment was acturally present in their F1 offspring's genome.

Germ-line transmission of hFVIII(ΔB) exogenous DNA from transgenic animals to their F1 generation was confirmed by using PCR detection and direct PCR product sequencing. The sequencing result exhibited the transgenic hFVIII(ΔB) fragment was actually present in the F1 offspring genome of transgenic goats (FIG. 5).

EXAMPLE 3

Figure 6A:
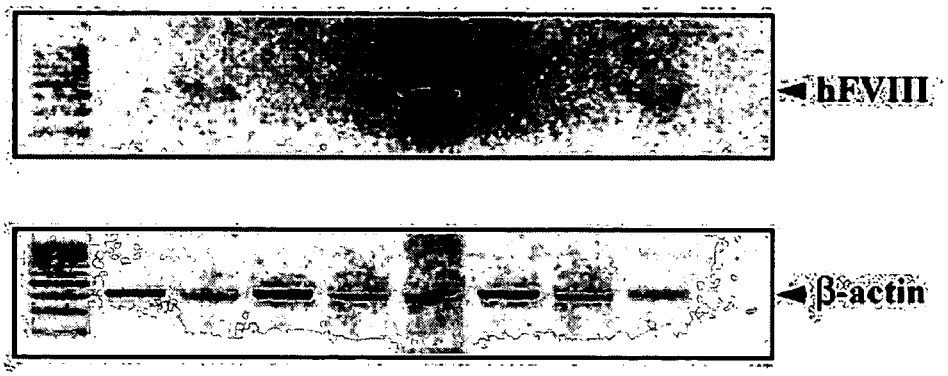
FIG. 6A~6B shows the mammary-specific expression cassette regulated a temporal and spatial expression of exogenous hFVIII RNA in transgenic animals.

Temporal and Spatial Expression of Exogenous hFVIII RNA in Transgenic Animals Driven by Mammary-Specific Expression Cassette To characterize the spatial expression of the new developed mammary-specific expression cassette containing hFVIII in this invention, total tissue RNAs were extracted from different organs in the breeding lines established from the transgenic founder mice. Reverse-transcriptional polymerase chain reaction (RT-PCR) analysis was performed using two pair of primer sets, one was phFVIII-F2(+) (SEQ ID NO:11) and phFVIII-R2(−) (SEQ ID NO: 12) specific to human FVIII cDNA franking 3'-coding region, the other was β-actin primer set as an internal control. As shown in FIG. 6A, the transgene expressed transcriptant of the 410-bp hFVIII RT-PCR product was found in the mammary gland of lactating transgenic mouse. No homologous transcripts were detectable in the heart (H), liver (L), lung (LU), muscle (M), brain (B), pancreas (P), or in male transgenic mouse mammary fat pads (F). All examined tissues showed a 420-bp amplified fragment for mouse β-actin to assess the integrity and quantity of RNA in each sample. The efficiency of DNase I treatment to eliminate DNA contamination was determined using RNA from a transgenic mammary gland. When the reverse transcriptase was omitted from the reaction, no amplification was observed (FIG. 6A, last lane).

Figure 6B:
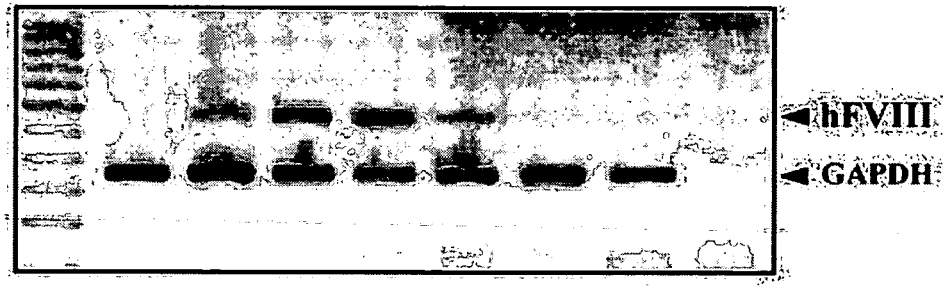

Temporal expression studies were performed on the F1 transgenic mice in the breeding lines established from founder mice αLAF-15 and -18. Total RNAs were extracted at different physiological states in the transgenic mammary gland using tissue biopsies subjected to RT-PCR detection. The results showed that the recombinant hFVIII mRNA was expressed in all lactating periods (D1, D8, D15 and D22, shown in FIG. 6B), whereas the same transcripts were not detectable in the later stages of pregnancy before parturition (D-3) and in the weaning stage after lactation (D29 and D36, in FIG. 6B). The 2.0-kb bovine αLA promoter had a highly tissue-specific and stage-specific gene regulation activity in the mammary epithelial cells during the lactation period.

To quantify the level of hFVIII mRNA in the mammary glands of transgenic mice, densitometric analysis was performed for comparing the intensity of the 250-bp band in each lane normalized to the level of signal generated upon co-amplification of the mouse glyceraldehyde-3-phosphate dehydrogenase (GAPDH) primers. The intensity of the hFVIII transcript increased eight-fold and ten-fold upon Day 8 and Day 15 post-parturition, respectively, whereas the intensity was decreased by two-fold on Day 22 of the later lactation (FIG. 6B) when compared to Day 1 of the newly lactating stage.

EXAMPLE 4

Figure 7A:
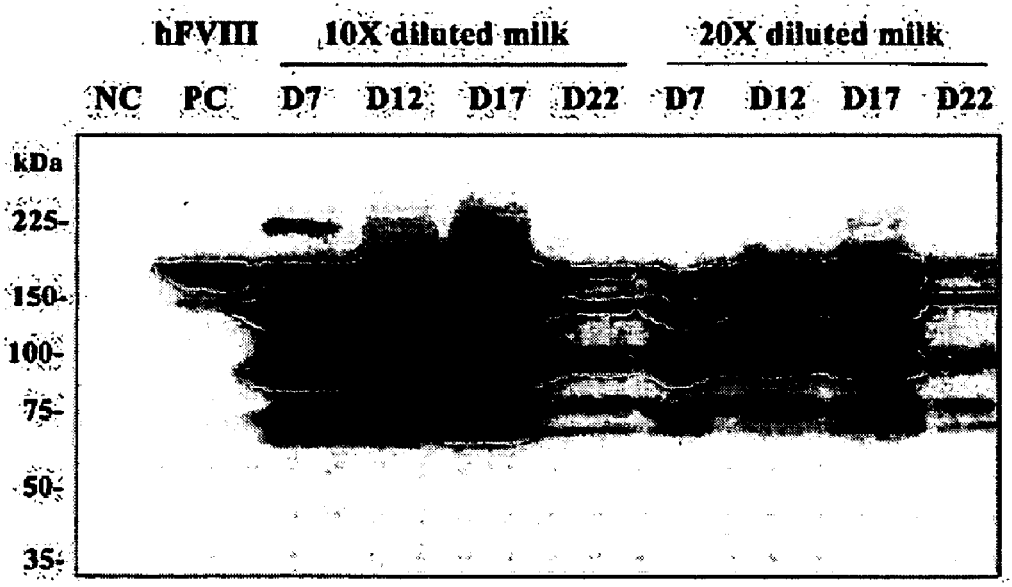
FIG. 7A~7B shows the Western blot analysis of recombinant hFVIII protein secreted from mammary glands of transgenic mice at different lactating stage.
Figure 7B:
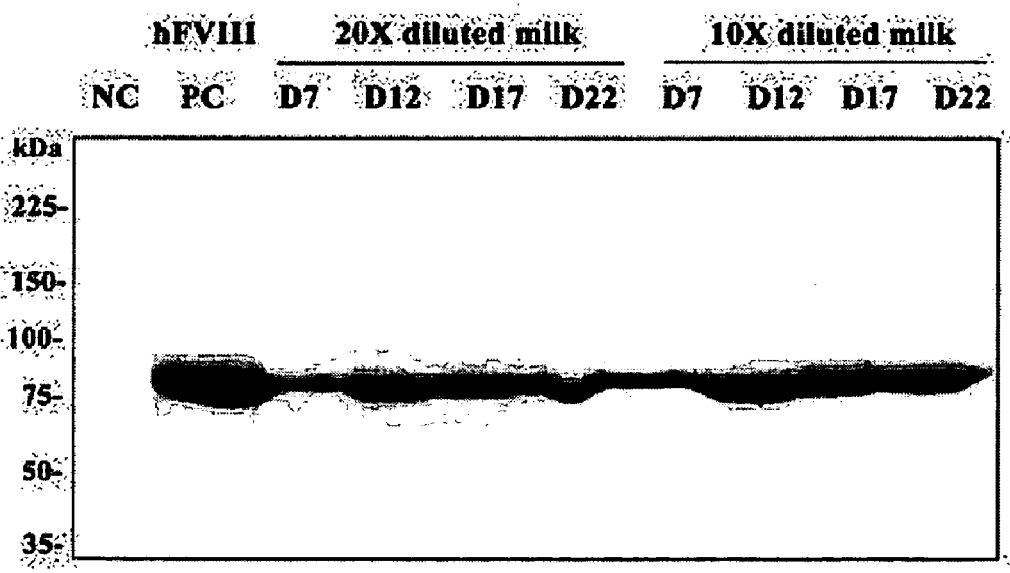

Expression and Secretion of Recombinant hFVIII Proteins into the Milk of Transgenic Animals To determine the production of recombinant hFVIII and to compare the secretion efficiency of rFVIII among different transgenic mouse lines, milk was collected from five lines of F0, F1 and F2 females during lactation. Proteins from skim milk of both non-transgenic control animals and transgenic animals were separated in SDS-PAGE and followed by Western blot analysis (FIG. 7A and 7B). No polypeptides characteristic of recombinant hFVIII were detected in control mouse milk using the hFVIII-specific polyclonal antibody. In the milk of transgenic animals, rFVIII was detected as a heterogeneous group of polypeptides of approximately 80-200 kDa, of which the 92-200 kDa polypeptides represent the heavy chain and its proteolytic cleavage products or different glycosylational modification patterns. The 80 kDa small molecule which correspond to the light chain containing hFVIII C2 domain was also detected by this antibody (FIG. 7A). Similar experiments were conducted using monoclonal antibodies that bind to specific hFVIII light chain C2 domain structures, and a specific polypeptide corresponding to a 80 kDa size was observed and compared with the HPLC-purified hFVIII C2 domain peptide (FIG. 7B).

Figure 8:
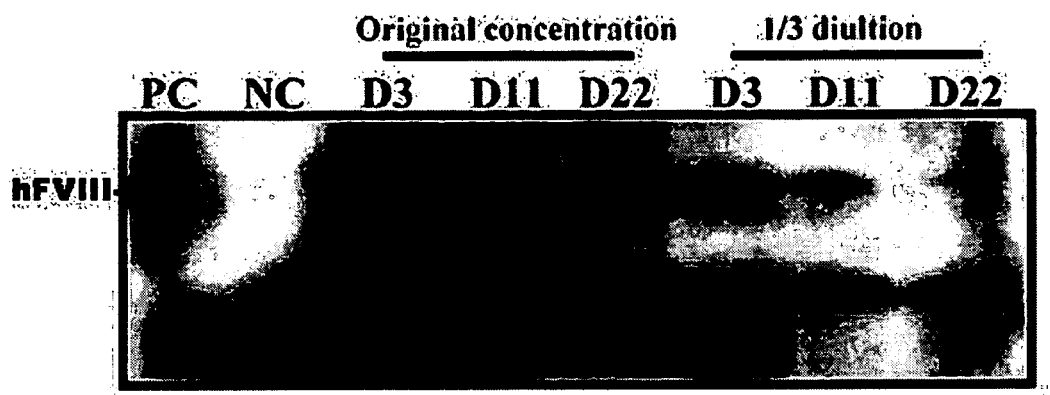
FIG. 8 shows the Western blot analysis of recombinant hFVIII protein secreted from mammary glands of transgenic goat (Tg-201) at early lactating stage. The secretion of rFVIII protein in milks was collected in days 3, 11 and 22. The collected milks were diluted in 1- to 3-fold and subjected to Western blotting and hybridization with rabbit anti-hFVIII polyclonal antiserum. Lane 1 contained HPLC-purified hFVIII heavy chain (200-kDa) as a positive control and lane 2 contained the milk protein harvested from non-transgenic mice during lactating stage as a negative control.

In the transgenic goat (Tg-201), milk was collected from days 3, 11 and 22 during early lactation stage for Western blot assay (FIG. 8). No polypeptides characteristic of recombinant hFVIII were detected in control goat milk using the hFVIII-specific polyclonal antibody. In transgenic milk, rFVIII was detected as a heterogenous group of polypeptides of approximately 80-200 kDa, which represent the heavy chain and its proteolytic cleavage products or different glycosylational modification patterns.

EXAMPLE 5

Biological Function Assay for Clotting Activity of Recombinant hFVIII Derived from the Milk of Transgenic Animals The coagulant activity of hFVIII was measured by reduction of the activated partial thromboplastin time (APTT) in a one-stage assay (Over, 1984, Scand J. Haematol. 41: 13-24.). Human FVIII dilutions equivalent to a 1:10 to 1:120 dilution of normal plasma were prepared in 50 mM imidazole buffer, pH 7.4, containing 100 mM sodium choride, 0.1% BSA and 0.01% Tween-20. Control and transgenic mouse milks diluted 1:20, 1:30, and 1:40 were incubated in duplicate at 37° C. in hFVIII-deficient plasma (Sigma Diagnostics, St. Louis, Mo.), followed by the automated addition of APTT reagent (Dade Behring, Marburg, Germany). Clot formation was initiated by the addition of 35 mM $CaCl_2$. The clot time, in seconds, was recorded on an ST2 Coagulometer (Stago). Semi-logarithmic analysis was used to plot the clot time versus amount of FVIII. Control mouse milk gave results similar to the reagent blank.

The concentrations of rFVIII ranged from 7.0 to 50.2 μg/ml, over 35- to 200-fold higher than that in normal human plasma (Table 1). The expression levels of rFVIII from three groups carrying low, middle and high copy numbers of transgenes were not significantly different. Recombinant hFVIII production generally tended to increase through the lactation period, but dropped dramatically at the end of lactation. This result was in parallel with the RNA transcript assay (FIG. 6A and 6B) as well as the typical mouse milk production curve, mouse milk yield increased throughout.

Figures 9A, 9B, 9C:
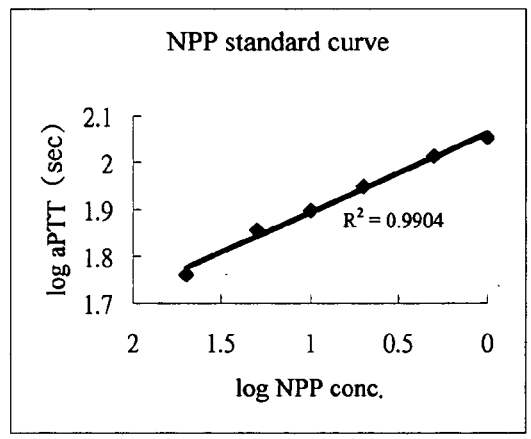
FIG. 9A~9C shows the functional assay of transgenic hFVIII protein by clotting activity analysis. The coagulant activity of hFVIII was measured by reduction of the activated partial thromboplastin time (aPTT) in a one-stage assay (Over, 1984, Scand J. Haematol. 41: 13-24.).

The functional activity of rFVIII was examined using one-stage clotting assays (Table 1) to demonstrate that rFVIII secreted in the milk of transgenic mice was biologically active. In the clotting assay, the addition of transgenic mouse milk, to FVIII-deficient human plasma resulted in the restoration of normal coagulant activity. Up to 13.41 U/ml of rFVIII procoagulant activity was detected. The activity of rFVIII was detected throughout lactation as shown in Table 1. The same result for rFVIII clotting activity derived from transgenic goat also has been demonstrated and shown in FIG. 9A to 9C.

TABLE 1

Recombinant hFVIII concentration and coagulation activity in the milk of transgenic animals with different groups of transgene copy, lines and generations

| No. of transgenic rFVIII concentration mice | Lactations and days (L/D) | Coagulation activity assay (U/ml)$^a$ | (μg/ml) |
|---|---|---|---|
| Low copy group (1-5 copies) | | | |
| aLAF15 (Fo) | L1/D7 | 4.82 ± 0.43 | 22.84 ± 1.65 |
| (n = 1) | L1/D12 | 7.11 ± 0.76 | 30.58 ± 1.37 |
| | L1/D19 | 3.60 ± 0.51 | 19.87 ± 0.96 |
| aLAF36 (F1) | L1/D7 | 6.38 ± 1.85 | 29.26 ± 3.58 |
| (n = 4) | L1/D17 | 5.64 ± 2.66 | 24.92 ± 3.04 |
| | L2/D7 | 13.41 ± 2.87 | 50.21 ± 5.73 |
| | L2/D17 | 9.46 ± 2.04 | 40.84 ± 4.91 |
| Middle copy group (10-20 copies) | | | |
| aLAF18 (F1) | L1/D7 | 0.98 ± 0.39 | 7.03 ± 2.56 |
| (n = 3) | L1/D12 | 6.14 ± 0.98 | 32.07 ± 4.30 |
| | L1/D17 | 8.91 ± 2.15 | 41.37 ± 7.78 |
| aLAF28 (F2) | L1/D7 | 3.01 ± 0.95 | 9.23 ± 3.74 |
| (n = 3) | L1/D12 | 6.55 ± 2.07 | 35.56 ± 6.08 |
| | L2/D17 | 7.81 ± 2.53 | 38.11 ± 5.72 |
| High copy group (40-50 copies) | | | |
| aLAF25 (F1) | L1/D8 | 11.28 ± 2.33 | 46.33 ± 4.57 |
| (n = 3) | L1/D15 | 8.72 ± 1.79 | 32.92 ± 3.97 |
| | L1/D21 | 1.56 ± 0.24 | 15.08 ± 4.84 |
| aLAF25 (F2) | L1/D8 | 7.92 ± 2.01 | 39.29 ± 6.89 |
| (n = 3) | L1/D15 | 8.58 ± 2.78 | 43.48 ± 5.21 |
| | L1/D21 | 1.22 ± 0.61 | 13.32 ± 5.05 |

$^a$One unit of rFVIII was defined as equivalent to the amount of human FVIII normally present in 1 ml of plasma, approximately 200 ng. Results presented are the average of two independent assays The Advantages of the Invention 1. The new developed mammary-specific expression cassette containing three important parts:

(1) 2.0-kb bovine αLA gene promoter which has been shown to be the most lactation-specific of all bovine milk protein genes;

(2) use of the αS1-CN 15-aa or αLA 19-aa as a secretary peptide to lead the rFVIII protein secretion; and (3) the bGH polyadenosylation signal to stabilize the steady-state of hFVIII RNA molecules, which can guaranty the highly expression and efficiently secretion of any exogenous proteins.

2. Transgenic expression delivers the advantages of mammalian cells such as a sophisticated refolding machinery and glycosylation.

3. Transgenic productions are scale-up flexibility since the herd size can be increased rapidly and inexpensively, as well as the relative low-cost and low complexity of the raw product manufacturing facilities as compared to more traditional cell culture facilities.

4. Biological active recombinant hFVIII protein derived from the milk of transgenic animals is easily collected by a diary automatic milk collection system and purified to obtain the massive recombinant protein.

5. Transgenic mice, goats and pigs expressing high levels of rFVIII either in full-length gene constructs or in B domain-deleted hFVIII will be a great value system for the mass production of biologically active rFVIII in transgenic farm animals.

The following sequence description and listing is further attached hereto as an appendix to this application as both a paper copy and a copy in computer readable form (CRF), with the sequence description and listing being in accordance with U.S. Patent and Trademark Office Rules and Regulations, as set forth in 37 CFR §1.821-1.825.

What is claimed is:

1. A non-human transgenic mammal selected from the group consisting of mice, rats, goats, pigs, sheep and cows, whose genome comprises:
   (a) an α-lactalbumin (α-LA) promoter; and
   (b) a nucleotide sequence operably linked to the α-LA promoter, the nucleotide sequence encoding a recombinant polypeptide comprising a B-domain deleted human clotting factor VIII polypeptide having the amino acid sequence of SEQ ID NO: 15,
   wherein the non-human transgenic mammal secretes the B-domain deleted human FVIII polypeptide in milk when the mammal is lactating.

2. A method for making the non-human transgenic mammal of claim 1, the method comprising:

(a) introducing into an embryo of a non-human mammal a transgene comprising
   (i) an α-lactalbumin (α-LA) promoter; and
   (ii) a nucleotide sequence operably linked to the α-LA promoter, the nucleotide sequence encoding a recombinant polypeptide comprising a B-domain deleted human clotting factor VIII polypeptide having the amino acid sequence of SEQ ID NO: 15,
(b) implanting the embryo into a female of the same species as the embryo; and
(c) permitting the embryo to develop into the non-human transgenic mammal of claim 1.

* * * * *